United States Patent [19]

Ainsworth et al.

[11] 4,396,627

[45] Aug. 2, 1983

[54] SECONDARY AMINES, THEIR PREPARATION AND USE IN PHARMACEUTICAL COMPOSITIONS

[75] Inventors: Anthony T. Ainsworth, Cranleigh; David G. Smith, Redhill, both of England

[73] Assignee: Beecham Group Limited, England

[21] Appl. No.: 357,992

[22] Filed: Mar. 15, 1982

Related U.S. Application Data

[63] Continuation of Ser. No. 157,556, Jun. 9, 1980, abandoned.

[30] Foreign Application Priority Data

Jun. 16, 1979 [GB] United Kingdom ................. 7921039

[51] Int. Cl.³ .................. A61K 31/24; A61K 31/135; C07C 87/28; C07C 101/30
[52] U.S. Cl. ..................................... 424/309; 424/311; 424/319; 424/321; 424/322; 424/324; 424/330; 560/12; 560/13; 560/21; 560/34; 560/42; 560/251; 560/252; 562/430; 562/435; 562/439; 562/451; 564/49; 564/51; 564/99; 564/157; 564/162; 564/165; 564/220; 564/361; 564/363

[58] Field of Search ...................... 564/49, 51, 99, 220, 564/157, 162, 165, 361, 363; 560/251, 252, 12, 13, 21, 34, 42; 562/430, 435, 439, 451; 424/309, 311, 319, 321, 322, 324, 330

[56] References Cited

U.S. PATENT DOCUMENTS 4,137,328 1/1979 Cox et al. ............................ 424/324

FOREIGN PATENT DOCUMENTS 1529972 7/1975 United Kingdom .
1520394 3/1977 United Kingdom .

Primary Examiner—Natalie Trousof
Assistant Examiner—L. Hendriksen
Attorney, Agent, or Firm—Jacobs & Jacobs

[57] ABSTRACT

Compounds having the formula:

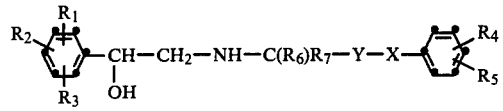

where $R_1$, $R_2$, $R_3$, $R_4$, $R_5$, Y and X are as defined hereinbelow, are useful for the reduction of abnormally high blood glucose and lipid levels in the treatment of obesity or hyperglycaemia.

15 Claims, No Drawings

SECONDARY AMINES, THEIR PREPARATION AND USE IN PHARMACEUTICAL COMPOSITIONS

CROSS-REFERENCE

This is a continuation of Ser. No. 157,556, filed June 9, 1980, now abandoned.

The present invention relates to a group of secondary amine derivatives that possess anti-obesity and anti-hyperglycaemic properties, to the method of their preparation and to their use as anti-obesity and/or anti-hyperglycaemic agents when formulated into a pharmaceutical composition.

Certain of the compounds within the formula (I):

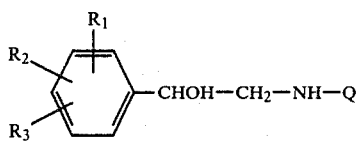

wherein $R_1$ is a hydrogen, fluorine or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R_2$ is a hydrogen, fluorine or chlorine atom or a hydroxyl group; $R_3$ is a hydrogen or chlorine atom or a hydroxyl group; and Q is an isopropyl or t-butyl group; are known to possess β-adrenoceptor agonist activity (see for example D. T. Collins et al, J. Med. Chem., 1970, 13, 674). Certain compounds within formula (I) wherein Q is a group such as a phenylaminoethyl were disclosed in Belgian Pat. No. 851232 as possessing β-adrenoceptor stimulant activity. Belgian Pat. No. 809831 disclosed that certain compounds within formula (I) wherein Q is inter alia a substituted phenylethyl group are useful as medicaments for the treatment of skin diseases. U.S. Pat. No. 3,818,101 disclosed certain compounds within formula (I) wherein Q could be inter alia an aralkyl group which may be used to induce polyphagia in meat producing animals. Certain compounds within the formula (I) wherein Q may be hydroxybenzyl or alkoxybenzyl group were indicated as possessing β-adrenergic stimulant and blocking properties in South African Pat. No. 67/5591. The preceding publications do not describe compounds of the formula (I) as possessing anti-obesity activity coupled with anti-hyperglycaemic activity nor indeed do they describe compounds of the formula (I) as possessing anti-obesity activity alone. We have discovered a group of compounds somewhat related to those of the formula (I) which possess anti-obesity properties and/or anti-hyperglycaemic properties. Such compounds may thus be used in the treatment of obesity or hyperglycaemia and can be envisaged as being of particular interest in conditions such as maturity onset diabetes where obesity is often linked with hyperglycaemia.

The present invention provides the compounds of the formula (II):

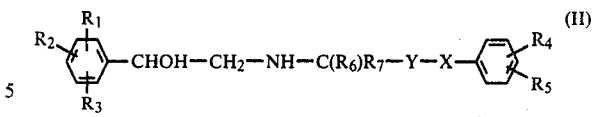

or a pharmaceutically acceptable salt thereof wherein $R_1$ $R_2$ and $R_3$ are as defined in relation to formula (I) or each independently represents a bromine atom; $R_4$ is an alkyl group of 1 to 10 carbon atoms substituted by a hydroxyl, lower alkoxyl, oxo, lower acyloxy or $OCH_2CO_2H$ group or lower alkyl ester thereof; $R_5$ is a hydrogen, chlorine or fluorine atom or a methyl, methoxyl or hydroxyl group or a carboxylic acid group or a salt, ester or amide thereof; $R_6$ is a hydrogen atom or a methyl, ethyl or propyl group; $R_7$ is a hydrogen atom or a methyl, ethyl or propyl group; X is an oxygen atom or a bond; and Y is an alkylene group of up to 6 carbon atoms or a bond.

When used herein the term "lower" means a group of 1 to 6 carbon atoms which is more suitably of 1 to 4 carbon atoms. When used herein the term "lower acyl" means a lower unsubstituted carboxylic acyl.

Preferred values for $R_1$ include the hydrogen, fluorine, chlorine and bromine atoms and the trifluoromethyl, hydroxymethyl, hydroxyl and amino groups.

Suitably X in the compound of the formula (II) is a bond. Preferred groups Y are of the formula $-(CH_2)_n-$ where n is an integer from 1 to 5, particularly 1 or 2.

A particularly suitable value for each of $R_2$ and $R_3$ is the hydrogen atom.

Particularly suitable groups $R_1R_2R_3C_6H_2$ include the phenyl; 2-fluorophenyl; 3-trifluoromethylphenyl; 3-chlorophenyl; 3,5-dichloro-4-aminophenyl; 2-chlorophenyl; 3-hydroxymethyl-4-hydroxyphenyl; 4-chlorophenyl; 3-bromophenyl and 3-fluorophenyl group.

A favourable value for $R_6$ is a hydrogen atom. A further favourable value for $R_6$ is the methyl group. A favourable value for $R_7$ is the hydrogen atom. A further favourable value for $R_7$ is the methyl group. Most favourably $C(R_6)R_7$ is a $CH_2$, $CHCH_3$, or $C(CH_3)_2$ group. The compounds of this invention wherein $C(R_6)R_7$ is a $CH_2$ or $C(CH_3)_2$ group tend to be less potent as anti-obesity agents than those wherein $C(R_6)R_7$ is a $CH(CH_3)$ group but since they possess one less centre of asymmetry they offer the advantage of a slightly easier synthesis. The compounds wherein $C(R_6)R_7$ is a $CH(CH_3)$ group offer the considerable advantage of higher potency as anti-obesity agents.

The point of attachment of the group $R_4$ is aptly meta- or para-to the point of attachment of the phenyl group to the rest of the molecule.

In order to optimise the anti-obesity effectiveness of the compounds of this invention it is desirable that $R_4$ is in the position para- to the point of attachment of the phenyl group to the rest of the molecule.

A preferred group $R_4$ is straight lower alkyl group substituted by a hydroxyl group A further preferred group $R_4$ is straight lower alkyl group substituted by a lower alkoxyl group.

Another preferred group $R_4$ is a straight lower alkyl group substituted by oxo or a lower acyloxyl group.

A particularly suitable group, $R_4$ is a methyl or ethyl group substituted by a hydroxyl, lower alkoxyl, oxo or, lower acyloxyl group or a salt or lower alkyl ester thereof.

One highly suitable group $R_4$ is the hydroxymethyl group.

A further highly suitable group $R_4$ is the methoxymethyl or oxoethyl group.

One group of preferred compounds of this invention are those of the formula (III):

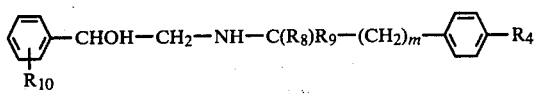

or a pharmaceutically acceptable salt thereof wherein $R_{10}$ is a hydrogen, fluorine, bromine or chlorine atom, or a trifluoromethy group, $R_8$ is a hydrogen atom or a methyl group; $R_9$ is a hydrogen atom or a methyl group; m is 1 or 2; and $R_4$ is as defined in relation to formula (II).

Preferably, $R_8$ and $R_9$ are simultaneously a hydrogen atom and a methyl group respectively.

A further group of preferred compounds of this invention are those of the formula (IV):

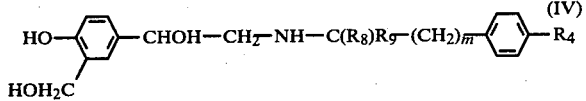

or a pharmaceutically acceptable salt thereof wherein $R_8$ is a hydrogen atom or a methyl group; $R_9$ is a hydrogen atom or a methyl group; m is 1, 2 or 3; and $R_4$ is as defined in relation to formula (II).

Preferably, $R_8$ and $R_9$ are simultaneously a hydrogen atom and a methyl group respectively. Suitably m is 1 or 2.

Most suitably $R_4$ in relation to the compounds of formula (III) and (IV) is a hydroxymethyl or methoxymethyl or oxoethyl group.

The compounds of this invention may be provided as acid addition salts. Such salts may be of an organic or inorganic acid but are normally salts with a pharmaceutically acceptable acid. Suitable acid addition salts include those formed with acids such as hydrochloric, hydrobromic, orthophosphoric, sulphuric, methanesulphonic, toluenesulphonic, acetic, propionic, lactic, citric, fumaric, malic, succinic salicylic, acetylsalicylic or the like acid.

The compounds of the formula (II) have a centre of asymmetry at the carbon atom marked with a single asterisk in formula (IIa):

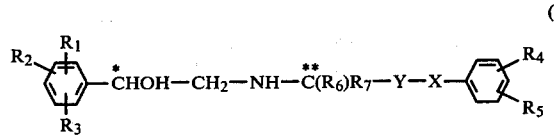

wherein $R_1-R_7$, Y and X are as defined in relation to formula (II). The compounds of the formula (II) have another centre of asymmetry at the carbon atom marked with two asterisks in formula (IIa) when $R_1-R_7$, Y and X are as defined in relation to formula (II) when $R_6$ is different from $R_7$.

The present invention extends to the individual stereoisomeric forms of the compounds of the formula (II) as well as to mixtures thereof. Aptly those compounds of the formula (II) which contain two asymmetric centres are provided in the form of the separated diastereoisomers or enantiomers thereof. Such separated diastereoisomers will of course contain a pair of enantiomers.

The preferred enantiomers are those having the R absolute configuration at the C* atom and the S absolute configuration at the C** atom.

X-Ray analysis may be used to determine and correlate absolute stereochemistry.

It has been observed that in the $^{13}C$ NMR of a compound containing a methyl group on the carbon atom $\alpha$ to the nitrogen atom (ie one existing in diastereoisomeric forms), the R*, R**; S*, S** diastereoisomer is that in which said methyl group appears at higher field (lower numerical value when expressed in ppm, typically <20 ppm downfield from tetramethylsilane) in $d_6DMSO$ solution, whilst the lower field (higher numerical value, typically $\geq 20$ ppm downfield from TMS) resonance is attributable to the $R^*, S^{**}; S^*, R^{**}$ modification. The amount of each diastereoisomer may be estimated from the relative intensities of the absorption lines and is expressed in the examples as a ratio (R* R**, S* S**:R* S**, S* R**). Other paired resonances can occur for the carbon atoms attached directly to the nitrogen atom and the carbon $\beta$ to nitrogen which carries the hydroxyl group.

The present invention also provides a pharmaceutical composition which comprises a compound of this invention and a pharmaceutically acceptable carrier.

The compositions of this invention will normally be formulated for oral administration although composition formulated for non-oral modes of administration, for example, injection, are also envisaged.

Particularly suitable oral dosage forms are unit dose forms such as tablets or capsules. Other fixed unit dose forms such as powders presented in sachets may also be used.

In accordance with conventional pharmaceutical practice the carrier may comprise a diluent, binder, filler, disintegrant, wetting agent, lubricant, colourant, flavourant or the like.

Typical carriers may therefore comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.01 to 500 mg, more usually 0.2 to 100 mg and favourably 0.5 to 50 mg. Such doses may be taken one to six times a day in a manner such that the total daily dose for a 70 kg adult will generally be about 0.1 to 500 mg and more usually about 1 to 100 mg. The more potent preferred compounds will generally be in unit doses containing 0.1 to 10 mg and more usually 0.25 to 5 mg. Their daily dose will generally be about 0.5 to 20 mg, more usually 1 to 10 mg, for example 2 to 5 mg.

In addition to use in human medicine the compositions of this invention may be used to treat obesity in domestic mammals such as dogs. In general administration to domestic mammals may be by mouth and will usually take place one or two times a day at about 0.025 mg/kg to 25 mg/kg, for example 0.1 mg/kg to 5 mg/kg.

The present invention also provides a process for the preparation of a compound of this invention which comprises the reduction of a compound of the formula (V):

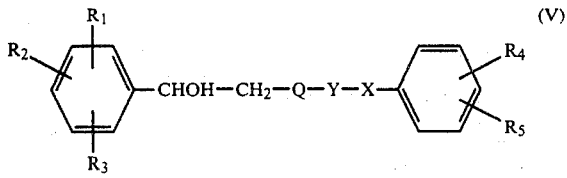

(V)

wherein Q is a —N=CR$_6$ or —NH—C(OH)R$_6$— group and R$_1$, R$_2$, R$_3$, R$_4$, R$_5$, R$_6$, Y and X are as defined in relation to formula (II) and thereafter if desired forming an addition salt of the initially produced compound of the formula (II).

The reduction of the compound of formula (V) may be normally effected by catalytic hydrogenation. Suitable catalysts include noble metal catalysts such as palladium, for example palladium on charcoal or the like such as platinum for example as platinum oxide.

If platinum is used as catalyst an atmospheric pressure of hydrogen may be employed. The reaction may be carried out at any convenient nonextreme temperature but it is generally most suitable to use an ambient or a slightly super ambient temperature such as 30° C. to 100° C., for example 40° C. to 80° C. The hydrogenation may be carried out in a conventional hydrogenation solvent such as a lower alkanol, for example ethanol.

The desired compound may be isolated from the reaction mixture by evaporation of the filtered solution. The initially obtained product may be purified by conventional means, for example by chromatography, crystallisation or the like.

The reduction of the compound of the formula (V) may also be effected using a complex hydride such as sodium borohydride.

This reduction is generally carried out in a lower alkanolic solvent, for example methanol.

An approximately ambient temperature may be employed, for example 20° to 30° C.

The desired compound may be obtained from the reaction mixture by evaporation, extraction into a suitable solvent such as ethyl acetate and evaporation. The initially obtained product may be purified as outlined hereinbefore.

The compound of the formula (V) may be prepared by the reaction of a compound of the formula (VI):

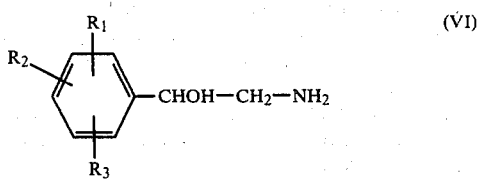

(VI)

wherein R$_1$, R$_2$ and R$_3$ are as defined in relation to formula (II) with a compound of the formula (VII):

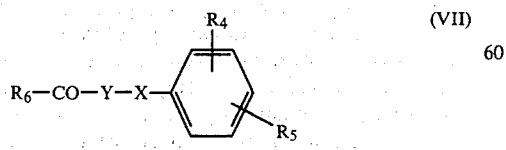

(VII)

wherein R$_4$, R$_5$, R$_6$, Y and X are as defined in relation to formula (II).

The condensation reaction is generally carried out under conditions that result in the removal of water formed during the reaction. A convenient method is to remove azeotropically the water from a refluxing benzene solution using a Dean and Stark apparatus.

It is often convenient to prepare and utilize the compound of the formula (V) in situ without isolation. In this case the reaction may comprise the hydrogenation of a mixture of a compound of the formula (VI) and a compound of the formula (VII) wherein R$_1$, R$_2$, R$_3$, R$_4$, R$_5$, R$_6$, X and Y are as defined in relation to formula (II).

Such a hydrogenation may be carried out under conditions as described for the hydrogenation of a compound of the formula (V).

The compounds of the formula (II) as hereinbefore defined may also be prepared by the reaction of a compound of the formula (VIII):

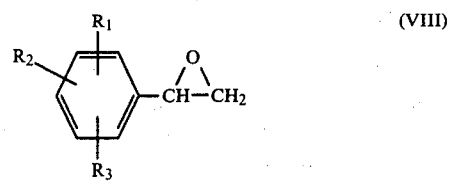

(VIII)

wherein R$_1$, R$_2$ and R$_3$ are as defined in relation to formula (II) with a compound of the formula (IX)

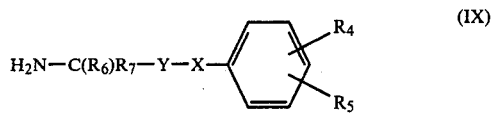

(IX)

wherein R$_4$, R$_5$, R$_6$, R$_7$, X and Y are as defined in relation to formula (II).

This reaction may be carried out in a protic solvent such as a lower alkanol, preferably ethanol.

A further method of preparing the compounds of the formula (II) comprises the reduction of a compound of the formula (X):

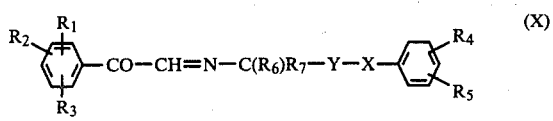

(X)

wherein R$_1$, R$_2$, R$_3$, R$_4$, R$_5$, R$_6$, R$_7$, X and Y are as defined in relation to formula (II).

The reduction of the compound of the formula (X) may be carried out using a borohydride or the like as described for the reduction of the compound of the formula (V).

The compound of the formula (X) may be prepared by the reaction of a compound of the formula (XI):

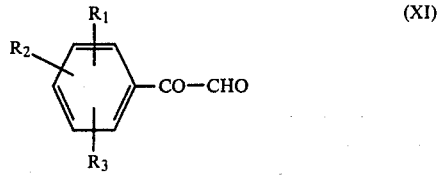

(XI)

or its hydrate or hemi-acetal of a lower alkanol wherein R$_1$, R$_2$ and R$_3$ are as defined in relation to formula (II), with a compound of the formula (IX) wherein R$_4$, R$_5$, $R_6$, $R_7$, X and Y are as defined in relation to formula (II).

The preceding reaction is generally carried out under the same conditions as that between compounds of formulae (VI) and (VII), i.e. with azeotropic removal of water using a Dean and Stark apparatus.

The compound of the formula (X) may be obtained from the reaction mixture by evaporation of the solvent and is normally used without further purification.

Another method of preparing the compounds of the formula (II) comprises the hydrogenation of a compound of the formula (XII)

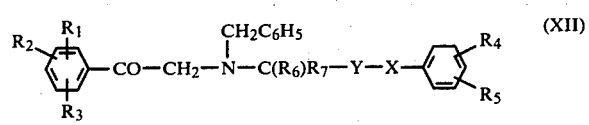

wherein $R_1$, $R_2$, $R_3$, $R_4$, $R_5$, $R_6$, $R_7$, X and Y are as defined in relation to formula (II).

The hydrogenation of the compound of the formula (XII) may take place as described for hydrogenation of the compound of the formula (V).

The compound of the formula (XII) may be prepared by the reaction of a compound of the formula (XIII):

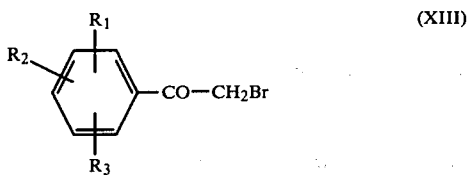

wherein $R_1$, $R_2$ and $R_3$ are as defined in relation to formula (II) with the N-benzyl derivative of a compound of the formula (IX).

This reaction may be carried out in a solvent such as acetonitrile or butanone at an elevated temperature, for example under reflux. An acid acceptor is generally present during the reaction for example a tertiary amine which may be a further mole of the N-benzyl derivative of the compound of the formula (IX).

After completion, the reaction mixture may be diluted with ether, filtered and the filtrate evaporated.

Yet another method of preparing compounds of formula (II) in which $R_4$ is a methyl group substituted by a hydroxyl group and $R_5$ is a hydrogen atom, comprises reducing a compound of formula (XIV):

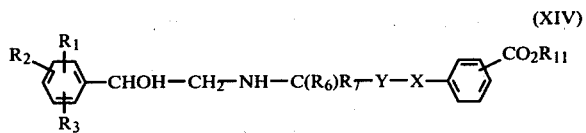

in which $R_1$, $R_2$, $R_3$, $R_6$, $R_7$, Y and X are as defined in formula (II), and $R_{11}$ is a lower alkyl group, with lithium aluminium hydride.

This reaction reduces the $CO_2R_{11}$ group to a hydroxy substituted methyl group, but does not effect the rest of the molecule.

Another method of preparing compounds of formula (II) comprises reducing a compound of formula (XV):

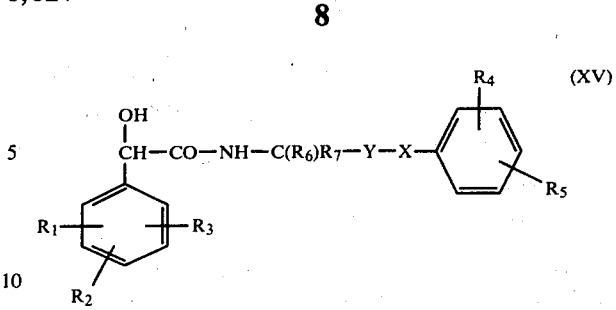

in which $R_1$ to $R_7$, X and Y are as defined in formula (II). This reduction may conveniently be carried out by using a complex metal hydride or diborane.

Compounds of formula (XV) may be prepared by reacting a compound of formula (XVI):

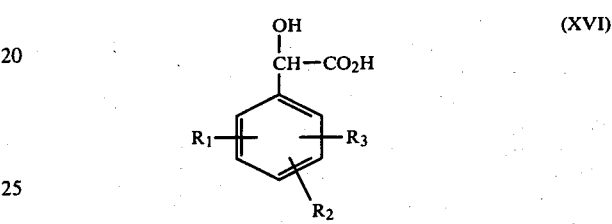

in which $R_1$, $R_2$ and $R_3$ are as defined in formula (II) with a compound of formula (IX) as defined above. The reaction may take place under standard peptide formation reaction conditions, for example in the presence of dicyclohexylcarbodi-imide, 1-hydroxybenztriazole and dimethylformamide.

By using single enantiomers of the compounds of formulae (XVI) and (IX) a stereospecific synthesis of single enantiomer of formula (II) can be achieved.

It will be appreciated that any groups which require protection in reactions will be protected in conventional manner during the reaction and thereafter de-protected in conventional manner. Groups $R_1$, $R_2$, $R_3$ and particularly $R_4$, may be modified after the preceding reactions if required; for example a benzyloxy group can be converted to a hydroxy group by hydrogenation, an ester can be hydrolysed to an acid, a benzyl ester can be hydrogenated to yield an acid, a salt of an acid can be esterified by reaction with a reactive chloride, bromide or tosylate, an acid can be esterified by reaction with a hydroxy compound under dehydrating conditions, amides may be prepared from an acid via an acid chloride or similar reaction. A further suitable protecting group are ketals which may be used to protect ketones and thereafter removed in conventional manner such as mild hydrolysis.

Compounds of the formula (II) containing only one centre of asymmetry may be resolved in known manner, for example using an optically active acid as a resolving agent. Compounds of the formula (II) containing two centres of asymmetry may be separated into their diastereoisomers by fractional crystallisation from a suitable solvent, for example from ethyl acetate. After such separation the individual components of the diastereoisomer may be obtained by resolution in known manner, for example using an optically active acid as a resolving agent.

Suitable optically active acids for use in resolution processes are described in Topics In Stereochemistry, Vol. 6, Wiley Interscience 1971, Allinger N. L. and Eliel W. L. eds.

Stereospecific synthesis may also be employed in order to obtain specific enantiomers. Thus, for example a single enantiomer of a compound of the formula (VI) may be used to react with a compound of the formula (VII) prior to borohydride or catalytic reduction. Similarly a single enantiomer of a compound of the formula (IX) (where $R_6$ is not the same as $R_7$) may be used with a compound of the formula (VIII). Similarly a single enantiomer of a compound of the formula (IX) (where $R_6$ is not the same as $R_7$) may be used to react with a compound of the formula (XI) or (XIII) prior to borohydride reduction. The specific enantiomers produced by these processes may then be separated by conventional means such as fractional crystallisation from a suitable solvent, for example ethyl acetate.

The following Examples illustrate the invention; and the following Descriptions illustrate the preparation of useful intermediates:

EXAMPLE 1

N-[2-(4-Hydroxymethylphenyl)-1-methylethyl]-2-hydroxy-2-(4-hydroxy-3-hydroxymethylphenyl)ethanamine A mixture of 1-(4-hydroxymethylphenyl)propan-2-one (1.64 g) and 2-hydroxy-2-(4-hydroxy-3-hydroxymethylphenyl) ethanamine (1.23 g) in ethanol (80 ml) was refluxed 0.5 hours, cooled to ambient temperature, platinum oxide (0.1 g) added and the mixture hydrogenated at 75 psi and 50°–60° for 8 hours. The solution was filtered, evaporated, the residue taken up in ethyl acetate and filtered again. Removal of the solvent gave the title compound as an oil which was finally obtained as a hard foam, (52:48 mixture of diastereoisomers) from ethyl acetate-benzene.

$\tau(d_6DMSO)$ 9.1 (3H, d, J=6 Hz), 7.0–7.85 (5H, m), 5.65 (2H, s+2H, s+1H, t), 4.9 (5H, broad), 2.5–3.4 (7H, m).

EXAMPLE 2

N-[2-(4-Methoxymethylphenyl)-1-methylethyl]-2-hydroxy-2-(4-hydroxy-3-hydroxymethylphenyl)ethanamine A mixture of 1-(4-methoxymethylphenyl)propan-2-one (0.46 g) and 2-hydroxy-2-(4-hydroxy-3-hydroxymethylphenyl) ethanamine (0.45 g) in ethanol (50 ml) was refluxed 0.5 hours, cooled to ambient temperature and hydrogenated at atmospheric pressure using platinum oxide as catalyst. The solution was filtered, evaporated, the residue taken up in ethyl acetate and filtered again. Removal of the solvent gave an oil which was crystallised and recrystallised from benzene to give the title compound, mp 81°–92°, as a 53:47 mixture of diastereoisomers.

$\tau(d_6DMSO)$ 9.13 (3H, d, J=7 Hz), 7.0–7.8 (5H, m), 6.8 (3H, s), 5.71 (2H, s), 5.56 (2H, s+1H, t), 4.0–5.5 (4H, broad), 2.7–3.41 (7H, m).

EXAMPLE 3

N-[2-(4-Hydroxymethylphenyl)-1-methylethyl]-2-hydroxy-2-phenyl ethanamine

A mixture of 1-(4-hydroxymethylphenyl)propan-2-one (3.0 g) and 2-hydroxy-2-phenylethanamine (2.5 g) in benzene (200 ml) was refluxed for 4 hours under Dean and Stark conditions. The solvent was replaced with ethanol (200 ml), platinum oxide (200 mg) was added and the mixture was hydrogenated at ambient temperature and pressure. The solution was filtered and evaporated to give an oil which was taken up in propan-2-ol and treated with the theoretical amount of fumaric acid. The title compound was obtained as the hemifumarate salt m.p. 67°–70° (60:40 mixture of diastereoisomers).

$\tau(d_6DMSO)$ 8.9 (3H, d, J=6 Hz), 6.5–7.6 (5H, m), 5.5 (2H, s), 5.15 (1H, m), 3.5 (2H, s), 2.3–3.0 (9H, m), 2.3 (5H, br, disappears with $D_2O$).

EXAMPLE 4

N-[2-(4-methoxymethylphenyl)-1-methylethyl]-2-hydroxy-2-phenyl ethanamine

The title compound was obtained as the hydrochloride salt m.p. 90°–105° (56:44 mixture of diastereoisomers) by the method of Example 3, replacing 1-(4-hydroxymethylphenyl)propan-2-one with 1-(4-methoxymethylphenyl)propan-2-one.

$\tau(d_6DMSO)$ 8.9 (3H, d, J=6 Hz), 6.5–7.8 (5H, m), 6.7 (3H, s), 5.6 (2H, s), 5.1 (1H, m), 3.5 (1H, s), 2.5–3.2 (9H, m), 2.3 (2H, d, J=8 Hz).

EXAMPLE 5

N-[2-(4-Acetoxymethylphenyl)-1-methylethyl]-2-hydroxy-2-phenylethanamine

The title compound was prepared as a 74:26 mixture of diastereoisomers m.p. 78°–82° by the process of Example 3, replacing 1-(4-hydroxymethylphenyl)propan-2-one with 1-(4-acetoxymethylphenyl)propan-2-one.

$\tau(CDCl_3)$ 9.0 (3H, d, J=6 Hz), 8.95 (3H, s), 7.0–7.6 (5H, m), 6.7 (2H, br), 5.4 (1H, m), 5.0 (2H, s), 2.5–3.0 (9H, m).

EXAMPLE 6

N-[2-(4-Acetylphenyl)-1-methylethyl]-2-hydroxy-2-phenylethanamine

A mixture of 1-(4-acetylphenyl) propan-2-one (10.9 g) and 2-hydroxy-2-phenylethanamine (8.5 g) in benzene (200 ml) was refluxed for 4 hours under Dean and Stark conditions. The solvent was replaced with ethanol (200 ml), platinum oxide (200 mg) was added and the mixture was hydrogenated at ambient temperature and pressure for 6 hours. The solution was filtered and the filtrate was evaporated and chromatographed on silica gel 60 (400 g) eluting with 1% methanol/chloroform. The first fraction (9.0 g) was crystallised from ether to give the title compound as a 9:91 mixture of diasteroisomers m.p. 120°–135°.

$\tau(CDCl_3)$ 8.95 (3H, d, J=6 Hz), 6.5 (3H, s), 6.9–7.6 (7H, m), 5.35 (1H, dd), 2.75 (2H, d, J=8 Hz), 2.7 (5H, s), 2.2 (2H, d, J=8 Hz). Evaporation of the mother liquors gave an oil which was dissolved in propan-2-ol and treated with the theoretical quantity of fumaric acid. Trituration with ether gave the title compound as the fumarate salt m.p. 88°–90° (84:16 ratio of diastereoisomers).

(DMSO $d_6$) 8.95 (3H, d, J=6 Hz), 7.4 (3H, s), 6.5–7.5 (5H, m), 5.2 (1H, m), 3.45 (1H, s), 2.3–3.3 (8H, m), 2.1 (2H, d, J=8 Hz). Elution with 2% methanol/chloroform gave a second fraction which was identified as N-[2-(4-[1-hydroxy-1-ethyl]phenyl)-1-methylethyl]-2-hydroxy-2-phenylethanamine (EXAMPLE 7), and was isolated as the hydrochloride salt m.p. 100°-2°.

$\tau(CDCl_3)$ 8.95 (3H, d, J=6 Hz), 8.65 (3H, d, J=6 Hz), 7.0–7.7 (7H, m), 6.3 (1H, m) 5.3 (1H, m), 2.6–3.0 (9H, m).

EXAMPLE 8

N-[2-(4-Hydroxymethylphenyl)-1-methylethyl]-2-(2-fluorophenyl)-2-hydroxy ethanamine The title compound was prepared as a 60:40 mixture of diastereoisomers, as the fumarate salt m.p. 169°–171° by the process of Example 3, replacing 2-hydroxy-2-phenylethanamine with 2-(2-fluorophenyl)-2-hydroxyethanamine.

$\tau$(free base) (CDCl$_3$), 9.0 (3H, d, J=6 Hz), 6.8–7.7 (5H, m), 5.45 (2H, s), 5.2 (1H, m), 2.4–3.2 (8H, m).

EXAMPLE 9

N-[3-(4-Hydroxymethylphenyl)-1-methylpropyl]-2-hydroxy-2-(3-trifluoromethylphenyl)ethanamine A solution of N-[3-(4-carbomethoxyphenyl)-1-methylpropyl]-2-hydroxy-2-(3-trifluoromethylphenyl) ethanamine (2.5 g) in dry ether (50 ml) was added to a suspension of lithium aluminium hydride (0.88 g) in dry ether (100 ml) under an atmosphere of nitrogen and the resulting mixture was boiled for 1 hour before being cooled and treated with water (0.9 ml); 2 N NaOH (1.8 ml) then water (2.7 ml) and stirred for a further hour.

The resulting precipitate was removed by filtration and the filtrate evaporated to give the title compound as a colourless oil.

$\tau$(CDCl$_3$): 8.92 (3H, d), 8.33 (2H, m), 7.00–7.69 (8H, m), 5.41 (2H, s), 5.30–5.50 (1H, m), 2.36–3.00 (8H, m).

The product was obtained as a 60:40 mixture of diastereoisomers, as the hydrobromide salt m.p. 109°–115°.

EXAMPLE 10

N-[3-(4-Hydroxymethylphenyl)-1-methylpropyl]-2-(3-chlorophenyl)-2-hydroxyethanamine The title compound was obtained as a colourless oil by the process of Example 9, replacing N-[3-(4-carbomethoxyphenyl)-1-methylpropyl]-2-hydroxy-2-(3-trifluoromethylphenyl)ethanamine with N-[3-(4-carbomethoxyphenyl)-1-methylpropyl]-2-(3-chlorophenyl)-2-hydroxyethanamine.

$\tau$(CDCl$_3$): 8.97 (3H, d), 8.40 (2H, m), 7.20–7.63 (5H, m), 6.68–7.15 (3H, m), 5.46 (2H, s), 5.50 (1H, m), 2.67–3.08 (8H, m).

The product was obtained as a 66:34 mixture of diastereoisomers, as the hydrobromide salt m.p. 122°–127°.

EXAMPLE 11

N-[2-(4-Hydroxymethylphenyl)-1-methylethyl]-2-(3-chlorophenyl)-2-hydroxy ethanamine The title compound was obtained as a colourless oil by the process of Example 9, replacing N-[3-(4-carbomethoxyphenyl)-1-methylpropyl]-2-hydroxy-2-(3-trifluoromethylphenyl) ethanamine with N-[2-(4-carbomethoxyphenyl)-1-methylethyl]-2-(3-chlorophenyl)-2-hydroxyethanamine and using dry tetrahydrofuran as solvent.

$\tau$(CDCl$_3$): 8.95 (3H, d, J=6 Hz), 7.0–7.7 (5H, m), 5.35 (2H, s), 5.2–5.6 (1H, m), 2.6–3.0 (8H, m).

The product was obtained as a 50:50 mixture of diasteroisomers, as the fumarate salt m.p. 123°–133°.

EXAMPLE 12

N-[2-(4-Hydroxymethylphenyl)-1-methylethyl]-2-hydroxy-2-(3-trifluoromethylphenyl) ethanamine The title compound was obtained as a colourless oil by the process of Example 9, replacing N-[3-(4-carbomethoxyphenyl)-1-methylpropyl]-2-hydroxy-2-(3-trifluoromethylphenyl) ethanamine with N-[2-(4-carbomethoxyphenyl)-1-methylethyl]-2-hydroxy-2-(3-trifluoromethylphenyl) ethanamine and using dry tetrahydrofuran as solvent.

$\tau$(CDCl$_3$): 8.9 (3H, d, J=6 Hz), 7.0–7.7 (5H, m), 5.35 (2H, s), 5.25–5.6 (1H, m), 2.35–3.0 (8H, m).

The product was obtained as a 52:48 mixture of diastereoisomers, as the fumarate salt m.p. 100°–2°.

EXAMPLE 13

N-[3-(4-Hydroxymethylphenyl)-1-methylpropyl]-2-hydroxy-2-phenylethanamine

The title compound was obtained as a colourless oil by the process of Example 9, replacing N-[3-(4-carbomethoxyphenyl)-1-methylpropyl]-2-hydroxy-2-(3-trifluoromethylphenyl) ethanamine with N-[3-(4-carbomethoxyphenyl)-1-methylpropyl]-2-hydroxy-2-phenylethanamine and using dry tetrahydrofuran as solvent.

$\tau$(CDCl$_3$): 9.0 (3H, d, J=6 Hz), 8.1–8.6 (2H, m), 7.2–7.6 (5H, m), 6.8 (2H, br, s), 5.45 (2H, s), 5.3–5.6 (1H, m), 2.65–3.1 (9H, m).

The product was obtained as a 50:50 mixture of diastereoisomers, as the fumarate salt m.p. 157–163.

EXAMPLE 14

(1R, 2'R; 1S, 2'S)-N-[2-(4-Hydroxymethylphenyl)-1-methylethyl]-2'-hydroxy-2'-phenylethanamine The title compound was obtained as a colourless oil by the process of Example 9, replacing N-[3-(4-carbomethoxyphenyl)-1-methylpropyl]-2-hydroxy-2-(3-trifluoromethylphenyl) ethanamine with (1R, 2'R; 1S, 2'S) N-[2-(4-carbomethoxyphenyl)-1-methylethyl]-2'-hydroxy-2'-phenylethanamine and using dry tetrahydrofuran as solvent.

$\tau$(CDCl$_3$): 8.95 (3H, d, J=6 Hz), 6.9–7.7 (5H, m), 5.40 (2H, s), 5.3–5.5 (1H, m), 2.6–3.0 (9H, m).

The product was obtained as the fumarate salt m.p. 73°–75° (>90% diastereoisomeric purity).

EXAMPLE 15

(1R, 2'S; 1S, 2'R)-N-[2-(4-Hydroxymethylphenyl)-1-methylethyl]-2'-hydroxy-2'-phenylethanamine The title compound was obtained as a colourless oil by the process of Example 9, replacing N-[3-(4-carbomethoxyphenyl)-1-methylpropyl]-2-hydroxy-2-(3-trifluoromethylphenyl)ethanamine with (1R, 2'S; 1S, 2'R)-N-[2-(4-carbomethoxyphenyl)-1-methylethyl]-2'-hydroxy-2'-phenylethanamine and using dry tetrahydrofuran as solvent.

$\tau$(CDCl$_3$): as in Example 14.

The product was obtained as the fumarate salt m.p. 113°–4° (>90% diastereoisomeric purity).

EXAMPLE 16

N-[1-S-2-(4-Hydroxymethylphenyl)-1-methylethyl]-2-R-2-hydroxy-2-phenylethanamine The title compound was obtained as a colourless oil by the process of Example 9, replacing N-[3-(4-carbomethoxyphenyl)-1-methylpropyl]-2-hydroxy-2-(3-trifluoromethylphenyl) ethanamine with N-[1-S-2-(4-carbomethoxyphenyl)-1-methylethyl]-2-R-2-hydroxy-2- phenylethanamine and using dry tetrahydrofuran as solvent.

$\tau$(CDCl$_3$): as in Example 14.

The product was obtained as the fumarate salt m.p. 50°–52°. (~90% diastereoisomeric purity). $\alpha_D^{20}$ 12.4° (Ethanol).

DESCRIPTION 1

1-(4-Hydroxymethylphenyl)propan-2-one 1-(4-Carbomethoxyphenyl)propan-2-one ethylene ketal (17.66 g) in dry ether was added dropwise over 1 hour and under nitrogen to lithium aluminium hydride (3 g) in dry ether. The mixture was then refluxed for 1 hour. Water (3 ml), 2 N sodium hydroxide solution (3 ml) and further water (9 ml) were added, the mixture filtered and the filtrate dried. Removal of the solvent gave an oil (13.95 g). This oil was taken up in acetone, 2.5 N hydrochloric acid added and the solution left for 16 hours. The mixture was extracted with ether and the combined organic layers dried. Removal of the solvent gave the title compound. $\tau$(CDCl$_3$) 7.9 (3H, s), 7.48 (1H, s, disappears with D$_2$O), 6.38 (2H, s), 5.4 (2H, s), 2.88 (2H, d, J=8 Hz), 2.7 (2H, d, J=8 Hz).

DESCRIPTION 2

1-(4-Carbomethoxyphenyl)propan-2-one ethylene ketal

A mixture of 1-(4-carbomethoxyphenyl)propan-2-one (17.3 g), ethan-1,2-diol (5.6 g) and p-toluenesulphonic acid (200 ml) in benzene (150 ml) was refluxed under a Dean and Stark head until the theoretical amount of water had been collected (ca. 4 hours). The solvent was evaporated and the residue was partitioned between sodium bicarbonate solution and ether. The ethereal extract was washed with water, dried, evaporated and distilled to give 15.7 g (74%), bp 136–140/1.5 mm.

DESCRIPTION 3

1-(4-Methoxymethylphenyl)propan-2-one 1-(4-Bromomethylphenyl)propan-2-one ethylene ketal (1.35 g) in methanol was added to sodium methoxide (from sodium (0.11 g)) in methanol containing a trace of sodium iodide. The mixture was refluxed for 1 hour. Methanol was removed, the residue partitioned between water and ether and the combined organic extracts dried. Removal of the solvent gave an oil which was dissolved in methanol-2 N hydrochloric acid and left for 1 hour at room temperature. Extraction with ether gave the title compound, bp 106°/0.7 mm. $\tau$(CDCl$_3$) 7.9 (3H, s), 7.63 (3H, s), 6.33 (2H, s), 5.54 (2H, s), 2.8 (2H, d, J=8 Hz), 2.6 (2H, d, J=8 Hz).

DESCRIPTION 4

1-(4-Bromomethylphenyl)propan-2-one ethylene ketal

A mixture of 1-(4-hydroxymethylphenyl)propan-2-one (3.15 g) and dibromotriphenylphosphorane (8.11 g) was refluxed in acetonitrile (50 ml) for 1 hour. The solvent was removed and the residue chromatographed on silica. Elution with ether gave 1-(4-bromomethylphenyl)propan-2-one, 3.4 g. $\tau$(CDCl$_3$) 7.92 (3H, s), 6.4 (2H, s), 5.6 (2H, s), 2.9 (2H, d, J=8 Hz), 2.65 (2H, d, J=8 Hz). This was ketalised in an analogous manner to that described in Description 2 to give the title compound, 3.73 g. $\tau$(CDCl$_3$) 8.7 (3H, s), 7.1 (2H, s), 5.9–6.3 (4H, m), 5.54 (2H, s), 2.75 (4H, s).

DESCRIPTION 5

1-(4-Acetoxymethylphenyl)propan-2-one

Acetyl chloride (5.0 ml) in dry ether (20 ml) was added dropwise to a stirred solution of 1-(4-hydroxymethylphenyl)propane-2-one ethylene ketal (3.0 g) (as prepared in description 1) in dry ether (50 ml). The mixture was refluxed for 1 h, evaporated and deketalised as described in description 1, to give the title compound as a colourless oil which was bulb distilled, bath temperature 120°–130°/o. 1 mm Hg.

$\tau$(CDCl$_3$): 7.9 (3H, s), 7.82 (3H, s), 6.3 (2H, s), 4.9 (2H, s), 2.6 (2H, d), 2.8 (2H, d).

DESCRIPTION 6

1-(4-Acetylphenyl) propan-2-one

1. 1-Phenylpropan-2-ol

Sodium borohydride (10.0 g) was added portionwise to an ice cold stirred solution of 1-phenylpropan-2-one (30.0 g) in methanol (500 ml). The mixture was stirred for 4 hours, evaporated and partitioned between water (100 ml) and chloroform (200 ml). The organic phase was dried (MgSO$_4$) and evaporated to give the product as a colourless oil (26.4 g).

$\tau$(CDCl$_3$): 8.95 (3H, d, J=6 Hz), 7.4 (2H, d, J=6 Hz), 7.15 (1H, d, disappears with D$_2$O), 5.9–6.4 (1H, m), 2.7–3.1 (5H, m).

2. 2-Acetoxy-1-phenylpropane

Acetyl chloride (16.7 g) in dry ether (50 ml) was added dropwise to a stirred solution of 1-phenylpropan-2-ol (26.4 g) in dry ether (250 ml). The mixture was refluxed for 2 h, washed with sodium bicarbonate solution, dried (MgSO$_4$) and evaporated to a colourless oil (27.5 g).

$\tau$(CDCL$_3$): 8.85 (3H, d, J=6 Hz), 8.05 (3H, s), 6.8–7.5 (2H, m), 4.5–5.2 (1H, m), 2.5–3.0 (5H, m).

3. 2-Acetoxy-1-(4-acetylphenyl)propane

2-Acetoxy-1-phenylpropane (5.2 g) in acetyl chloride (20 ml) was added dropwise to a stirred solution of aluminium chloride (16.0 g) and acetyl chloride (4.2 ml) in dichloroethane (150 ml). The mixture was stirred at ambient temperature for 72 hours, poured on to ice (500 g) and the organic phase was separated. The organic phase and washings were washed with sodium bicarbonate solution, dried (MgSO$_4$) and evaporated to an oil. Chromatography of the oil on alumina, eluting with ether/petrol gave the title compound (4.5 g).

$\tau$(CDCl$_3$): 8.80 (3H, d, J=6 Hz), 8.1 (3H, s), 7.4 (3H, s), 6.9–7.4 (2H, m), 4.7–5.1 (1H, m), 2.7 (2H, d, 8 Hz), 2.1 (2H, d, J=8 Hz).

4. 1-(4-Acetylphenyl) propan-2-ol

2-Acetoxy-1-(4-acetylphenyl) propane (4.5 g) was heated for 2 hours in refluxing 2 N sodium hydroxide solution. The mixture was allowed to cool and the product was extracted into ether. Evaporation of the dried (MgSO$_4$) extracts gave an oil (3.8 g).

(CDCl$_3$): 8.85 (3H, d), 7.55 (3H, s), 7.2 (2H, d, J=6 Hz), 6.9 (1H, br, s, disappears with D$_2$O), 5.8–6.2 (1H, m), 2.7 (2H, d, J=8 Hz), 2.1 (2H, d, J=8 Hz).

5. 1-(4-Acetylphenyl) propan-2-one

Chromic acid solution (11.5 ml, made by adding sulphuric acid [7.3 ml] to sodium dichromate [10.0 g] in water [30 ml] and making up to 50 ml with water) was added to a vigorously stirred solution of 1-(4-acetylphenyl) propan-2-ol (3.8 g) in ether (50 ml) keeping between 25°–30°. The mixture was stirred at ambient temperature for 2 hours, the organic phase was separated, washed with sodium bicarbonate solution and with saturated sodium chloride solution. The dried (MgSO$_4$) solution was evaporated and distilled (2.5 g). b.p. 122°–128°/0.1 mm.

τ(CDCl$_3$): 7.8 (3H, s), 7.4 (3H, s), 6.2 (2H, s), 2.7 (2H, d, J=8 Hz), 2.1 (2H, d, J=8 Hz).

DESCRIPTION 7

2-(2-Fluorophenyl)-2-hydroxyethanamine

Trimethylsilyl cyanide (8.5 g) was added to a stirred mixture of 2-fluorobenzaldehyde (10.6 g) and zinc iodide (500 mg) in dry ether (150 ml). The mixture was stirred at ambient temperature for 24 hours and was then added dropwise to a stirred suspension of lithium aluminium hydride (3.2 g) in dry ether (50 ml) under nitrogen. The mixture was refluxed for 2 hours, cooled and water (3.2 ml), 2 N sodium hydroxide solution (3.2 ml) and water (9.6 ml) slowly added. The precipitate was filtered off, the filtrate was dried (MgSO$_4$) and evaporated to a yellow oil (13.0 g) which crystallised slowly on standing.

τ(CDCl$_3$): 7.6 (3H, br. s disappears with D$_2$O), 6.9–7.4 (2H, m), 5.0–5.2 (1H, m), 2.4–3.2 (4H, m).

DESCRIPTION 8

N-[3-(4-Carbomethoxyphenyl)-1-methylpropyl]-2-hydroxy-2-(3-trifluoromethylphenyl) ethanamine A mixture of 4-(4-carbomethoxyphenyl) butan-2-one (3.0 g) and 2-hydroxy-2-(3-trifluoromethylphenyl) ethanamine (3.0 g) in dry benzene (100 ml) was refluxed under Dean and Stark conditions for 2 hours. The solvent was replaced with methanol (100 ml) and sodium borohydride (2.0 g) was added portionwise with ice cooling. The mixture was stirred at ambient temperature for 2 hours, the solvent was evaporated and the residue was partitioned between water (100 ml) and chloroform (100 ml). The organic phase was dried (MgSO$_4$) and evaporated to an oil, which was chromatographed on silica gel 60 in 3% methanol/chloroform. The title compound was obtained as a colourless oil.

τ(CDCl$_3$): 8.9 (3H, d, J=6 Hz), 8.1–8.5 (2H, m), 6.9–7.6 (7H, m) 6.1 (3H, s), 5.3 (1H, m), 2.0–2.9 (8H, m).

The product was obtained as a 55:45 mixture of diastereoisomers, as the hydrochloride salt m.p. 147.5°–150.5°.

DESCRIPTION 9

2-Hydroxy-2-(3-trifluoromethylphenyl)ethanamine

The title compound was obtained as a yellow oil by the process of description 7, replacing 2-fluorobenzaldehyde with 3-trifluoromethylbenzaldehyde.

τ(CDCl$_3$): 7.7 (3H, br. s, disappears with D$_2$O), 6.9–7.5 (2H, m), 5.2–5.5 (1H, m), 2.3–2.6 (4H, m).

DESCRIPTION 10

N-[3-(4-Carbomethoxyphenyl)-1-methylpropyl]-2-(3-chlorophenyl)-2-hydroxyethanamine The title compound was obtained as a 52:48 mixture of diastereoisomers, as the hydrochloride salt m.p. 143°–8° by the process of description 8, replacing 2-hydroxy-2-(3-trifluoromethylphenyl) ethanamine with 2-(3-chlorophenyl)-2-hydroxyethanamine.

τ(CDCl$_3$): (free base): 8.9 (3H, d, J=6 Hz), 8.1–8.6 (2H, m), 7.0–7.6 (7H, m), 6.1 (3H, s), 5.4 (1H, m), 2.6–2.9 (6H, m), 2.1 (2H, d, J=8 Hz).

DESCRIPTION 11

2-(3-Chlorophenyl)-2-hydroxyethanamine

The title compound was obtained as a yellow oil by the process of description 7, replacing 2-fluorobenzaldehyde with 3-chlorobenzaldehyde.

τ(CDCl$_3$): 7.3–7.5 (2H, m), 7.1 (3H, br. s, disappears with D$_2$O), 5.4–5.7 (1H, m), 2.6–3.0 (4H, m).

DESCRIPTION 12

N-[2-(4-carbomethoxyphenyl)-1-methylethyl]-2-(3-chlorophenyl)-2-hydroxyethanamine The title compound was prepared as described in our copending British Patent Application No. 7937084.

DESCRIPTION 13

N-[2-(4-Carbomethoxyphenyl)-1-methylethyl]-2-hydroxy-2-(3-trifluoromethylphenyl) ethanamine The title compound was obtained as a 50:50 mixture of diastereoisomers, as crystals from ether m.p. 73°–83° by the process of description 8, replacing 4-(4-carbomethoxyphenyl) butan-2-one with 1-(4-carbomethoxyphenyl) propan-2-one.

τ(CDCl$_3$): 8.9 (3H, d, J=6 Hz), 6.9–7.5 (7H, m), 6.1 (3H, s), 5.2–5.5 (1H, m), 2.4–2.9 (6H, m), 2.1 (2H, d, J=8 Hz).

DESCRIPTION 14

N-[3-(4-carbomethoxyphenyl)-1-methylpropyl]-2-hydroxy-2-phenylethanamine

The title compound was obtained as a 49:51 mixture of diastereoisomers, as crystals from heptane m.p. 109°–119° by the process of description 8, replacing 2-hydroxy-2-(3-trifluoromethylphenyl)ethanamine with 2-hydroxy-2-phenylethanamine.

τ(CDCl$_3$): 8.9 (3H, d, J=6 Hz), 8.2–8.5 (2H, m), 7.8 (2H, br. s, disappears with D$_2$0), 6.9–7.5 (4H, m), 6.1 (3H, s), 5.2–5.5 (1H, m), 2.5–2.8 (7H, m), 2.1 (2H, d, J=8 Hz).

DESCRIPTION 15

Separation of diastereoisomers of N-[2-(4-carbomethoxyphenyl)-1-methylethyl]-2-hydroxy-2-phenylethanamine A mixture of 2-hydroxy-2-phenylethanamine (17.7 g) and 1-(4-carbomethoxyphenyl) propan-2-one (24.8 g) in ethanol (300 ml) was refluxed for one hour. When cooled, 10% Pd/C (1.0 g) was added and the mixture was hydrogenated on a Parr Hydrogenator at 60° and 60 psi for six hours. The mixture was filtered and the filtrate was evaporated to an oil which was taken up in methanol (75 ml). The solution was allowed to stand at 4° to give crystals (Batch 1). Ether (75 ml) was added to the mother liquors to obtain subsequent crops (Batches 2 & 3). The mother liquors were evaporated to an oil, which was crystallised from ether (Batch 4).

| BATCH | m.p. | WEIGHT | DIASTEREOISOMER RATIO % | |
|---|---|---|---|---|
| | | | (1R,2'R; 1S,2'S) | (1R,2'S; 1S,2'R) |
| 1 | 110-122 | 7.85 | 11 | 89 |
| 2 | 110-123 | 1.96 | 12.5 | 87.5 |
| 3 | 108-124 | 2.6 | 15 | 85 |
| 4 | 82-90 | 8.2 | 89.5 | 10.5 |

Recrystallisation of Batch 1 from methanol gave colourless crystals of (1R,2'S;1S,2'R)-N-[2-(4-carbomethoxyphenyl)-1-methylethyl]-2'-hydroxy-2'-phenylethanamine m.p. 124-124.5 (92% diastereoisomeric purity).

Recrystallisation of Batch 4 from water gave colourless crystals of (1R,2'R;1S,2'S)-N-[2-(4-carbomethoxyphenyl)-1-methylethyl]-2'-hydroxy-2'-phenylethanamine m.p. 89°-91° (97% diastereoisomeric purity).

DESCRIPTION 16

N-[1-S-2-(4-Carbomethoxyphenyl)-1-methylethyl]-2-R-hydroxy-2-phenylethanamine The title compound was obtained as colourless crystals from methanol m.p. 105° (95% enantiomeric purity) $\alpha_D^{20} - 29.5°$ (acetone) by the process of description 15, replacing 2-hydroxy-2-phenylethanamine with 2-R-2-hydroxy-2-phenylethanamine and isolating the high melting point enantiomer by crystallisation from methanol as described in description 15.

DEMONSTRATION OF EFFECTIVENESS OF COMPOUNDS (i) The compounds were dosed daily in water or carboxymethylcellulose suspension to genetically obese mice by oral gavage for 28 days. At the end of the time the carcass composition was determined. The results obtained were as follows:

| COMPOUND OF EXAMPLE | DOSE mg/kg p.o. | g-LIPID PER MOUSE | |
|---|---|---|---|
| | | TREATED | CONTROL |
| 1 | 9 | 19.0 | 21.7 |
| 2 | 9 | 18.9 | 20.7 |
| 3 | 11 | 17.3 | 21.3 |
| 4 | 9.4 | 17.3 | 20.7 |
| 6 (9:91) | 8.3 | 17.6 | 19.2 |
| 7 | 8.4 | 18.5 | 20.7 |
| 5 | 9.3 | 16.2 | 20.0 |

(ii) HYPOGLYCAEMIC ACTIVITY

Femal CFLP mice, weighing approximately 25 g, were fasted for 24 hours prior to the study. The compounds under study were dosed orally (20 mg and 5 mg/kg) to each of 8 mice. 30 minutes later a blood sample (20 ml) was obtained from the tail for the analysis of blood glucose. Immediately after taking this blood sample, each mouse was given a glucose load (1 g/kg body weight subcutaneously). Blood samples were then obtained from each mouse at 30 minute intervals for 120 minutes.

Compounds that produced a significant (P<0.05) reduction of blood glucose, compared with control mice given water, at any time interval were considered active. The area under the blood glucose curve over the 2 hour period after giving the glucose load was calculated for each compound and compared with the value for control animals. Thus a compound would give a 100% reduction in the area under the blood glucose curve if the blood glucose was maintained at the same level as in untreated fasted animals. Reduction in the glucose curve of more than 100% indicate that a compound, in spite of being given a glucose load, maintained blood glucose levels below that found in control fasted mice.

| COMPOUND OF EXAMPLE | DOSE mg/kg p.o. | REDUCTION IN AREA UNDER BLOOD GLUCOSE CURVE (%) |
|---|---|---|
| 1 | 5 | 162 |
| 2 | 5 | 106 |

(iii) CARDIAC ACTIVITY

Rat hearts were perfused by the Langendorff procedure. Hearts were dissected free within 30 seconds of death and reverse perfused via the aorta and coronary vessels with Krebs-Ringer bicarbonate solution (pH 7.4 37° C.) gassed with 95% $O_2$:5% $CO_2$. The flow rate was between 8-12 mls/minute. Responses were obtained after injection of drug dissolved in isotonic saline into the perfusion media. Heart rate and tension were displayed on an Ormed MX2P recorder via a tension transducer and heart ratemeter.

Results are expressed as a percentage of the response due to salbutamol.

| COMPOUND OF EXAMPLE | DOSE ADDED (μg) | HEART TENSION | HEART RATE |
|---|---|---|---|
| 3 | 10 | 90 | 90 |
| 4 | 10 | 100 | 100 |
| 6 (9:91) | 10 | 15 | 0 |
| 6 (84:16) | 10 | 20 | 20 |
| 7 | 10 | 50 | 40 |
| 12 | 10 | 40 | 25 |

We claim:

1. A compound of formula (II):

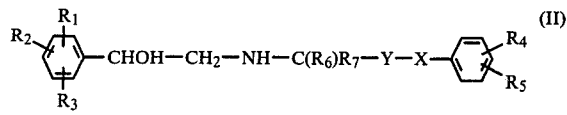

or a pharmaceutically acceptable salt thereof, in which $R_1$ is hydrogen, fluorine, chlorine, bromine, hydroxy, hydroxymethyl, methyl, methoxy, amino, formamido, acetamido, methylsulphonylamido, nitro, benzyloxy, methylsulphonylmethyl, uredio, trifluoromethyl or p-methoxybenzylamino; $R_2$ is hydrogen, fluorine, chlorine, bromine or hydroxyl; $R_3$ is hydrogen, chlorine or bromine or hydroxyl, $R_4$ is alkyl of 1 to 10 carbon atoms substituted by hydroxyl, lower alkoxyl, oxo, lower acyloxy, carboxymethyoxy or carbo(lower alkoxy)methoxy; $R_5$ is hydrogen, chlorine, fluorine, methyl, methoxy hydroxyl, or carboxy or lower alkyl ester or amide of said carboxy; $R_6$ is hydrogen, methyl, ethyl or propyl; $R_7$ is hydrogen, methyl, ethyl or propyl; X is a bond; and Y is alkylene of up to 6 carbon atoms or a bond.

2. A compound according to claim 1 in which $R_1$ is hydrogen, fluorine, chlorine, bromine, trifluoromethyl, hydroxymethyl, hydroxyl or amino.

3. A compound according to claim 1, in which Y is —$(CH_2)_n$— in which n is 1 or 2.

4. A compound according to claim 1, in which —C(R$_6$)R$_7$— is CH$_2$, CHCH$_3$ or C(CH$_3$)$_2$.

5. A compound according to claim 1, in which R$_4$ is methyl or ethyl substituted by hydroxyl, lower alkoxyl, oxo or lower acyloxyl.

6. A compound according to claim 1 of the formula

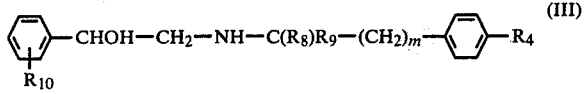

or a pharmaceutically acceptable salt thereof wherein R$_{10}$ is hydrogen, fluorine, bromine, chlorine, or trifluoromethyl, R$_8$ is hydrogen or methyl; R$_9$ is hydrogen or methyl; m is 1 or 2; and R$_4$ is as defined in claim 1.

7. A compound according to claim 1 of the formula (IV):

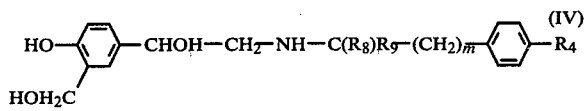

or a pharmaceutically acceptable salt thereof wherein R$_8$ is hydrogen or methyl; R$_9$ is hydrogen or methyl; m is 1, 2 or 3; and R$_4$ is as defined in claim 1.

8. A compound according to claim 1, in the form of a single stereoisomer.

9. A compound according to claim 1, in the form of a mixture of stereoisomers.

10. A compound according to claim 1, which contains two centres of asymmetry and is provided as a separated diastereoisomer.

11. A pharmaceutical composition for the reduction of abnormally high blood glucose and lipid levels in the treatment of obesity or hyperglycaemia, comprising an effective amount of a compound according to claim 1 in combination with a pharmaceutically acceptable carrier.

12. A composition according to claim 11 in unit dosage form.

13. A composition according to claim 12 in the form of tablets, pills, capsules, ampoules or sachets.

14. A method of reducing abnormally high blood glucose levels in the treatment of obesity or hyperglycaemia in human or other animals which comprises administering thereto an effective amount of a compound according to claim 1.

15. A method of reducing abnormally high blood lipid levels in the treatment of obesity or hyperglycaemia in humans or other animals which comprises administering thereto an effective amount of a compound according to claim 1.

* * * * *